United States Patent [19]

Heyman

[11] Patent Number: 4,571,239
[45] Date of Patent: Feb. 18, 1986

[54] CATHETER-STYLET ASSEMBLY FOR SLIPOVER URETHRAL INSTRUMENTS

[76] Inventor: Arnold M. Heyman, 3573 Terrace View Dr., Encino, Calif. 91436

[21] Appl. No.: 671,055

[22] Filed: Nov. 13, 1984

Related U.S. Application Data

[63] Continuation of Ser. No. 550,231, Nov. 8, 1983, abandoned, which is a continuation of Ser. No. 379,480, May 18, 1982, abandoned, which is a continuation-in-part of Ser. No. 353,432, Mar. 1, 1982, abandoned.

[51] Int. Cl.$^4$ ............................................. A61M 25/00
[52] U.S. Cl. ......................................... 604/54; 604/96; 604/165; 604/170; 604/280
[58] Field of Search ......................... 604/96, 164–166, 604/170, 264, 280, 282; 128/348.1

[56] References Cited

U.S. PATENT DOCUMENTS

| | | | |
|---|---|---|---|
| 3,297 | 10/1843 | Dodd | 128/311 |
| 2,118,631 | 5/1938 | Wappler | 604/170 |
| 2,856,934 | 10/1958 | Petillo | 604/170 |
| 3,918,450 | 11/1975 | Patel | 604/280 |
| 3,948,270 | 4/1976 | Hasson | 604/170 |
| 4,148,319 | 4/1979 | Kasper et al. | 604/170 |
| 4,155,364 | 5/1979 | Boxer | 604/96 |

OTHER PUBLICATIONS

Vlietstra, H. P., "New Possiblities for Ureteric Dilation", *Surgery*, vol. 37, No. 5, 5/1955, pp. 811–819.

*Primary Examiner*—C. Fred Rosenbaum
*Assistant Examiner*—Michelle N. Lester
*Attorney, Agent, or Firm*—Spensley Horn Jubas & Lubitz

[57] ABSTRACT

An elongated, hollow filiform having a tapered insertion tip is passed through the urethra to the urinary bladder and functions both as a probe to seek the lumen or opening of the urethra and as a guide so that a rigid, hollow stylet within a Councill catheter or the like can be slidably passed over the filiform into the bladder while the filiform remains in a stationary position within the urethra and the bladder. The stylet and the filiform can then be removed to leave the catheter within the bladder. If the urethra is constricted, a first elongated, hollow dilator can be guided over the filiform to dilate or widen the urethra before the stylet and catheter are introduced. If necessary, the first dilator can be replaced by a second dilator having a larger outer diameter to further dilate the urethra so that the diameter of the urethra will accommodate the Councill catheter containing the hollow rigid stylet.

17 Claims, 6 Drawing Figures

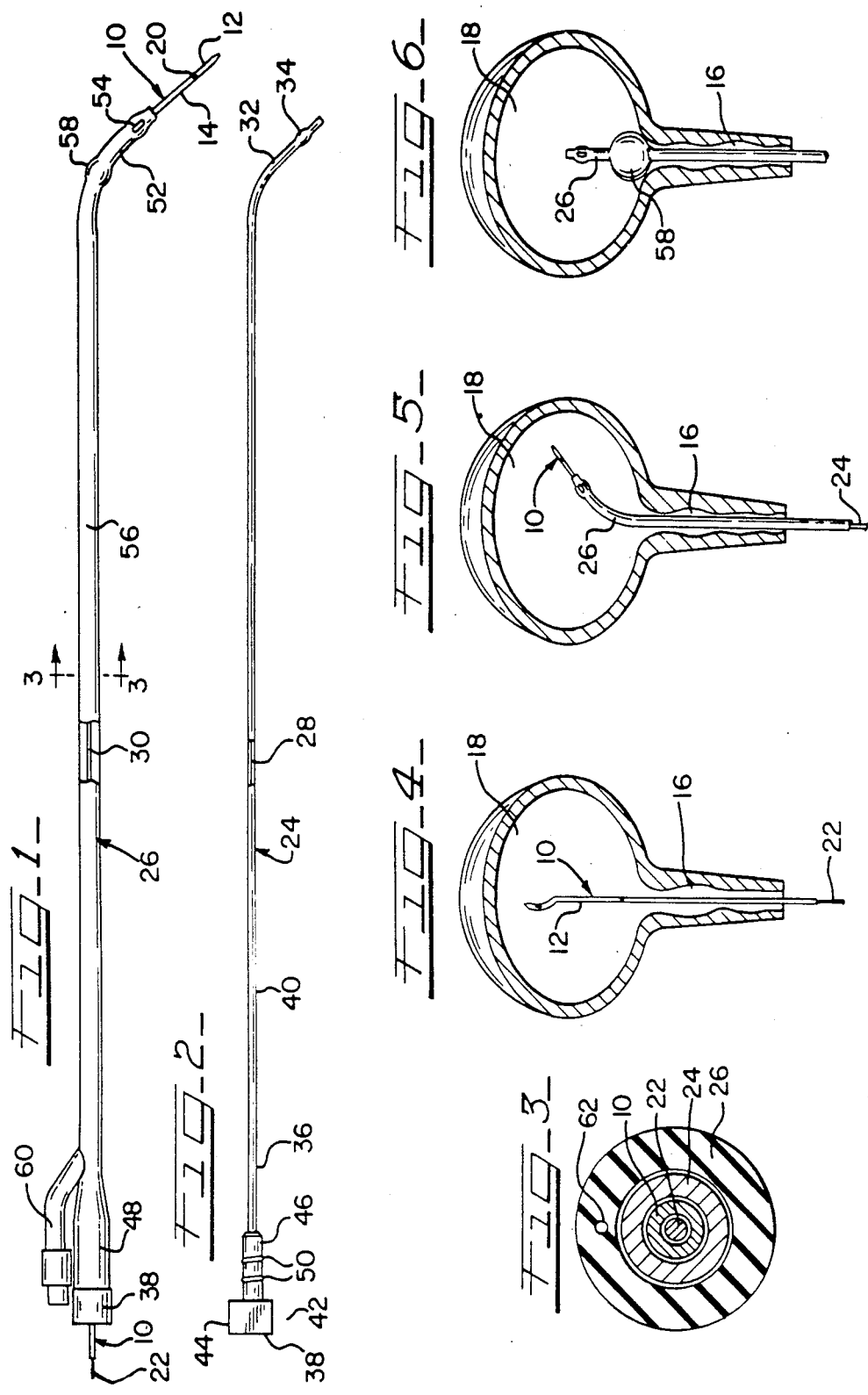

CATHETER-STYLET ASSEMBLY FOR SLIPOVER URETHRAL INSTRUMENTS

CROSS-REFERENCE TO A RELATED APPLICATION

This is a continuation of application Ser. No. 550231 filing date 11-08-83, now abandoned, which was a continuation of application Ser. No. 379480 filing date 5-18-82, now abandoned, which was a continuation-in-part of application Ser. No. 353,432, filed Mar. 1, 1982, now abandoned.

BACKGROUND OF THE INVENTION

The present invention and my copending applications relate generally to instruments for dilating a body passage to enable draining a fluid through the passage; and, in particular, the tubular instruments adapted to pass through the urethra to the urinary bladder for (1) dilating a narrowed urethra, (2) withdrawing urine, (3) inserting urethral instruments including retention catheters into the urinary tract or (4) performing urologic surgery.

The present invention specifically relates to a rigid, hollow stylet for insertion within a flexible, hollow catheter having an open tip portion—the stylet cooperates with a filiform to place the catheter in the bladder. The stylet can also be used without the filiform for placement of catheters that do not have open tip portions.

By way of background, the size of most urologic instruments including catheters, filiforms, followers, bougies and sounds is determined by the outer diameter of the instrument. Although there are both American and English scales of measurement, the Charriere or French (F) scale is most frequently used. According to the French scale, the size of a tubular instrument is determined by multiplying the diameter expressed in millimeters (mm) by 3. Thus, a diameter of 8 mm is equal to No. 24 F.

Catheters, as defined herein, are hollow, tubular instruments made of rubber, nylon, silicone, Teflon, woven silk (stiffened by shellac), plastic or metal that are used for drainage of fluid media, specifically urine, from the bladder. Many different types are available from a straight tube for a single insertion to tubes of varying shapes, curves and diameters for specific situations. All catheters, however, have similar functions—to provide drainage, to introduce medications and radiopaque contast media, and to obtain a urine specimen.

Catheters may be nonretentive or retentive. The most frequently used straight, nonretentive catheters are the Robinson and the whistle-tip design which are usually made of natural or latex rubber. The Robinson catheter has a solid rounded tip and may have two, four or six eyes or holes along its side. The whistle-tip catheter has an open tip portion and two eyes, one on the side and one at the semirounded angle of the tip. Robinson catheters have the disadvantage of being nonretentive but are used for a single insertion such as in the collection of a urine specimen or in relieving the patient of acute bladder retention.

Another type of nonretentive urethral catheter is the Coude catheter, also known as the "elbow" or "natural curve" catheter. The term "Coude", of course, refers only to the curve of the catheter tip, that tip usually includes a single eye and may taper to a point or have an olive-shaped enlargement (olive tip). The advantage of this curve is that it can following the contour of the bulbar and prostatic urethra as it curves beneath the symphysis pubis and rides over the bladder neck. Coude catheters are usually made of red rubber, are somewhat stiffer than Robinson catheters and are often impregnated with small amounts of lead for radiographic observation.

The most frequently used retentive catheter for draining the bladder is the Foley type, which comprises two tubes—a larger tube for drainage and a smaller side tube connected to a balloon that is inflated with a fluid after the catheter is positioned. The inflated balloon thus prevents the catheter from slipping out. A Councill catheter is similar to a Foley catheter, but includes an open tip portion that receives a special stylet which can be threadably connected to a filiform. The tip of the Foley and Councill catheter usually includes one or two eyes between the tip and the balloon. The present invention relates to an improved Councill catheter-stylet combination in which the filiform and stylet are not threadably connected.

As stated in my copending application, a catheter can usually be passed through the urethra without incident. Occasionally, however, particularly when the lumen of the urethra is narrowed because of disease or when a large tube such as a cystoscope or a large catheter is to be passed, the urethra may have to be dilated. This is done by inserting and withdrawing a series of progressively larger dilation instruments (dilators).

The most common dilator is a solid smooth metal instrument with a curved tip, called a sound, that looks like a metal catheter. For example, the Van Buren sound is such a solid metal instrument—but it is not intended to be left indwelling.

A bougie can also be used. A bougie is a slender, flexible, cylinder solid instrument having an enlarged tip portion for introduction into the urethra or other tubular organ, usually for the purpose of calibrating and dilating a constricted area.

If the passage is severely constricted, use of a filiform and a follower may be necessary. A filiform is a narrow, solid, somewhat stiff instrument commonly used to traverse a strictured urethra. Various filiform tips can be used, such as a straight, spiral or olive tip. The end of the filiform opposite the tip includes a female threaded portion. The follower, a semi-flexible catheter or bougie with a male threaded tip, is then threadably connected to the threaded portion of the filiform to define a tapered assembly having the appearance of a flexible whip.

The assembly can be guided through the strictured area and followers of an increasing diameter can be attached to the filiform upon withdrawal of the follower from the urethra to further dilate the stricture. As the follower is introduced, the filiform merely coils on itself inside the bladder. The screw-on filiform may have either a male or female thread and, of course, the follower must have a corresponding thread to be of use. Frequently the assembly must be left indwelling, particularly when it is desirable to dilate the urethra gradually over the course of several days. In that case, since the filiform is a solid shaft, eyes are provided in the sides of the catheter follower at the tip end portion to permit the drainage of urine from the bladder.

In a similar manner, a filiform can be threadably connected to a solid metal stylet for passage through the urethra. The stylet can be used to pass a catheter through a strictured urethra. In practice, the solid stylet is inserted within the catheter so that the threaded tip of the stylet extends beyond the open tip portion of the catheter, and the stylet can be threadably connected to the filiform. The filiform, stylet and catheter are then passed through the urethra to the bladder. Once the tip of the catheter is in the bladder, a balloon or an inflatable portion near the tip can be inflated to secure the catheter in position. Thereafter the filiform-stylet assembly is withdrawn.

Problems frequently arise, however, in the use of a threaded filiform-follower (or filiform-stylet) assembly. For example, the threaded connection can break or the follower (or the stylet) can separate from the filiform after insertion. In that case, it is very difficult to extricate the filiform from the bladder. Such removal can be performed endoscopically, or surgery may be required to open the bladder and gain sufficient access for removal. In addition to this serious disadvantage, the currently used threaded assembly is nondisposable and must be sterilized after each use. Moreover, the operation of connecting the threaded portion of the filiform and the follower or the stylet is awkward and time consuming.

DESCRIPTION OF THE PRIOR ART

In addition to the previously described urologic instruments, the following references constitute the closest prior art of which applicant is aware.

U.S. Pat. No. 2,856,934 to Petillo relates to a catheter consisting of a solid, flexible filiform and hollow, rigid follower. That reference does not show a hollow filiform or a hollow stylet for urethral catheter insertion. Moreover, the solid filiform of Petillo increases in diameter along its length such that a mid-length, the filiform measures 6 F. Since the hollow, rigid follower will only accommodate a filiform measuring 5 F or less, the complete length of the solid filiform cannot freely pass through the follower and the follower cannot pass all the way over the filiform. According to the present invention, a hollow filiform has a uniform diameter throughout its length to permit urethral instruments to slidably pass over the filiform for introduction into or removal from the urethra while the filiform remains positioned within the urinary tract. This enables an interchangeability of urological instruments not suggested by Petillo. Also, the filiform can be removed to leave the retention catheter in the bladder.

U.S. Pat. No. 3,811,449 to Gravlee et al. discloses a dilating apparatus which permits the insertion of a medical instrument into a body passage while the opening to the passage is maintained in a dilated state larger than the diameter of the instrument. An elongated, solid flexible probe having a uniform diameter and a rounded insertion tip is inserted into the passage. A first elongated, flexible, hollow dilator is inserted over the probe up to the insertion tip of the probe. The solid probe is then removed and a second elongated, flexible hollow dilator having a slightly larger internal diameter than the external diameter of the first dilator is inserted coextensive over the first dilator. In this manner, dilators having a successively greater internal diameter are sequentially inserted over dilators of lesser diameter and the smaller, inner dilators are removed from the passage until the tissue is stretched to a predetermined size by a final dilator.

The Gravlee device, however, is designed for use in dilating the cervical canal. Although Gravlee et al. mention the use of the probe and dilators to enlarge the urinary tract, that device is not suitable for urethral insertion and for use with urethral instruments such as a catheter, cystoscope or urethrotome. First, the probe is solid rather than hollow; and the external and internal diameters of the probe are large relative to the filiform of the present invention. Second, the leading ends of the probe and the dilator are not tapered or narrow enough to serve as a guide through the strictured urethra.

According to the present invention, it is essential that the filiform be small or narrow enough to pass within a catheter such as a Councill catheter, and its stylet. Moreover, the filiform must be narrow and have a tapered or rounded tip to prevent injury to the urethral mucosa during passage. Use of an extremely narrow filiform as a guide maintains the continuity of the urethra when catheters are changed after the damage urethra has been surgically repaired.

SUMMARY OF THE INVENTION

The present invention relates to the use of elongated filiforms or guides with slipover instruments and, in particular, to an improved catheterstylet combination. The device of my copending application comprises an elongated hollow filiform which is passed through the urethra to probe, seek and follow the passage. If the urethra is particularly difficult to traverse, a metal wire, also called a stylet, can be inserted within the filiform to increase the stiffness of the filiform during placement. Thereafter, the operator can insert a hollow dilator over the filiform while the filiform remains within the urethra.

The filiform serves as a guide for the subsequent insertion of instruments having various diameters into the urinary tract to dilate or calibrate the urethra. Indeed, the filiform can be used with most followers and sounds provided that the dilators are hollow through their length to form an opening slightly larger than the outer diameter of the filiform at the distal and proximal ends thereof. The hollow filiform also helps prevent false passages and the curling of the filiform in the urethra by permitting the operator to remove the wire stylet from the filiform and check for drainage or urine so that the operator will note when the tip of the filiform is in the bladder.

The present invention involves an improved catheterstylet for use with the above-described filiform. The stylet is particularly suited for use in the described slipover concept.

Specifically, the elongated, hollow filiform having a tapered insertion tip is passed through the urethra to the urinary bladder and functions both as a probe to seek the lumen or opening of the urethra and as a guide so that a rigid, hollow stylet within a Councill catheter or the like can be slidably passed over the filiform while the filiform remains in a stationary position in the urethra and bladder. The stylet and the filiform can then be removed to leave the catheter within the bladder. If the urethra is severely constricted, a first elongated, hollow dilator can be guided over the filiform to dilate or widen the urethra before the stylet and catheter can be replaced by a second dilator having a larger outer diameter to further dilate the urethra without removal of the filiform from the passage.

It follows, therefore, that it is an object of this invention to provide a device for passage to the bladder through the urethra wherein the device can be assembled in a simple and efficient manner and disengaged for separation of one part from the other for easy removal without the danger of breakage. The egress or aspiration of urine through the filiform indicates the location of the filiform tip within the bladder. False passages and curling of the filiform can be prevented because the operator can determine when the filiform tip enters the bladder. Moreover, the slipover concept permits a more orderly interaction between urologic instruments.

It is a related object to provide a hollow stylet for use in combination with the filiform and a hollow catheter having an open tip portion such as a Councill catheter wherein easy access can be had for assembly of the parts in a simple and efficient manner. The stylet can also be used without the filiform for placement of catheters that do not have open tip portions including Foley catheters.

These and other objects and advantages of this invention will hereinafter appear and for purposes of illustration, but not of limitation, in the accompanying drawings.

BRIEF DESCRIPTION OF THE INVENTION

FIG. 1 is a side view of a flexible catheter passed coaxially over the stylet and a hollow filiform;

FIG. 2 is a side view of the stylet;

FIG. 3 is a cross-sectional view taken along the line 3—3 of FIG. 1;

FIG. 4 is a schematic view showing a hollow filiform having a tapered tip passed through the urethra into the bladder;

FIG. 5 is a schematic view showing the catheter and stylet slidably passed over the filiform; and FIG. 6 is a schematic view showing the filiform member and stylet withdrawn, leaving a Councill catheter in position to drain the bladder.

DETAILED DESCRIPTION OF THE INVENTION

The present invention relates to the use of an elongated, hollow filiform as a guide for a catheter-stylet assembly. The invention replaces standard filiform and catheter stylets now available which use a threaded locking mechanism to connect the filiform to the stylet.

Referring to FIG. 1, the device includes a filiform 10 in the form of an elongated, hollow, flexible member having a relatively small cross section with a rounded or tapered end portion 12 on its proximal end 14 to facilitate insertion through the urethra 16 (see FIG. 4) and to avoid sharp edges which might traumatize the tissue of the urethra. The filiform 10 can be made into a variety of types, such as a straight member of uniform cross section or the proximal end 14 can be in the form of a spiral tip, an olive tip or the like. The filiform is dimensioned to have a length considerably greater than the distance between the bladder 18 and the external opening of the urethra.

In one embodiment, the filiform is 27 inches long and 4 F in diameter. Because of this small diameter, the filiform can be used to pass through the urethra and into the bladder. As indicated, the filiform is hollow and can be considered a filiform catheter since an opening 20 provide a passage for the drainage of fluid, such as urine from the bladder, and the injection of a radiopaque medium to determine the position of the filiform in the urinary tract. In addition, a metal wire or stylet 22 can be inserted within the filiform to provide the necessary stiffness and tactile sensation for passage of the hollow filiform through the urethra.

The present device also includes a stylet 24 and a catheter 26 in the form of elongated, hollow members, each having a passage 28 and 30, respectively, extending continuously therethrough. As used herein, the term "wire stylet" refers to the stylet 22 that passes within the filiform 10. The term "stylet", on the other hand, refers to the stylet 24 that is substantially larger in cross-section than the stylet 22 and which passes within the catheter 26.

Referring to FIG. 2, the stylet 24 is preferably made of a corrosion resistant metal and has a curved and tapered proximal end portion 32 for insertion through the catheter. An annular projection or bulbous portion 34 about the proximal end portion 32 expands the elastic inner wall of the catheter 26 to hold the stylet 24 within the catheter.

The distal end 36 of the stylet 24 includes a gripping portion 38 that is enlarged relative to the shaft 40 of the stylet. The gripping portion 38 is in the form of a cylinder with a flat surface 42 and a rounded surface 44 for holding by the thumb and forefinger of the user. Between the shaft 40 and the gripping portion 38 is a barrel-shaped portion 46 having a diameter slightly less than the inner diameter of the catheter to allow the distal end 48 of the catheter to rest over the barrel-shaped portion 46 and against the gripping portion 38. Annular rings 50 about the barrel-shaped portion assist in holding the distal end of the catheter in a fixed position on the stylet.

It can be seen that the gripping portion also functions as a means for preventing the proximal end portion 32 of the stylet 24 from passing beyond the proximal end portion 52 of the catheter 26; and that the length of the shaft is approximately equal to the length of the catheter. The catheter 26 has an opening in the proximal end portion 52 and includes at least one opening 54 through the side wall of the proximal end 52 to enable urine to drain from the bladder into the catheter. The catheter, like the stylet 24, is dimensioned to have a length slightly greater than the distance between the bladder and the entrance to the urethra but less than the length of the filiform 10. The proximal end 52 of the catheter can be formed to extend at an angle from the body portion 56, like a Coude catheter to facilitate insertion through the urethra; or the catheter can comrise a straight semi-flexible member.

In conventional practice, the catheter is generally made available in various cross-sectional dimensions to permit utilization of the maximum size catheter in the event that the passage through the urethra is very tight and to enable use of catheters of increasing cross section for replacement of one with another over a period of time as the obstruction through the urethra is relieved.

As described, the stylet 24 can be formed of a corrosion resistant, inert metal of the type used for surgical instruments to enable repeated use with sterilization procedures after each use. It is preferred to form the filiform of a plastic material as a single use, aseptic, disposable item.

An important concept of the invention resides in the ability of the hollow stylet 24 to freely slide over the filiform through the urethra and provide for removal of the filiform and the stylet while the catheter 26 remains in the passage. Equally important is the ability of the stylet 24 to move within the catheter 26. But the stylet tip cannot pass beyond the tip of the catheter and the catheter-stylet assembly must function as a unit during insertion with the stylet securely holding the catheter thereon. The interaction of these components can be more clearly seen in FIG. 3.

In use, the hollow filiform 10 is directed through the urethra until the tapered end portion 12 enters the bladder, as shown in FIG. 4. The filiform may coil on itself upon entering the bladder, and entry into the bladder is usually indicated by the egress or aspiration of urine through the filiform. If the urethra is particularly difficult to traverse, the wire stylet 22 can be inserted within the filiform to increase the stiffness of the filiform during placement.

Next, the stylet 24, which has been inserted within the catheter 26 is slidably passed coaxially over the filiform and into the urethra.

The hollow filiform 10 of the present invention offers several advantages and safety features over the solid filiforms of the prior art. For example, by observing the egress of urine from the filiform catheter once the wire stylet 22 is removed, one can safely conclude that the filiform tip is properly positioned in the bladder and the filiform is not in a false passage.

If the volume of effluent is insufficient, urine can be aspirated through the filiform with a syringe. Moreover, a radiograph can be taken to determine the position of the filiform tip by injecting a radiopaque contrast medium through the filiform. That was not possible with the filiforms of the prior art.

In the event that the stylet 24 and catheter cannot be advanced over the filiform for passage through the urethra, a hollow dilator of smaller cross section can be substituted. Once penetration has been established and the passage through the urethra is dilated the stylet and catheter can be substituted by removing the dilator without removal of the filiform and by passing the catheter-stylet assembly over the filiform and through the urethra into the bladder (see FIG. 4).

Therefore, the operation of inserting an indwelling catheter (such as a Councill catheter) involves (1) inserting a filiform catheter 10 through the urethra into the bladder, (2) dilating the urethra as necessary, (3) removing the dilator used and leaving the filiform in place, (4) inserting the stylet 24 into an open tip catheter, (5) slipping the catheter-stylet assembly over the filiform 10 into the bladder, (6) inflating a balloon 58 (see FIG. 6) of the catheter through a side port 60 (See FIG. 1) and (7) removing the filiform and the stylet. It will be noted that the balloon 58 is inflated in a conventional manner by injecting a fluid into the side port 60 once the proximal end portion 52 of the catheter is within the bladder. The fluid passes through a conduit 62 (FIG. 3) within the catheter to inflate the balloon.

Many other urologic instruments that are currently available can also be used with this device and method without modification. For example, a cystoscope with a direct vision obturator in place and without the lens will easily slip over the filiform. A cystoscope is an instrument specifically designed for passing through the urethra into the bladder to permit inspection of the interior of that organ. At the end of the cystoscope is an electric bulb or a fiberoptic lens system that illuminates the bladder interior, and a channel is provided to pass an irrigating fluid to distend the bladder. By means of special lenses the bladder mucosa can be examined for inflammation, calculi or tumors. A ureteral catheter can then be passed through the cystoscope into the bladder and beyond the bladder into the ureters and kidneys. In this manner, samples of urine can be obtained for diagnostic purposes of radiopaque fluids can be injected into the ureters for X-rays of the upper urinary tract.

In addition, the performance of urologic surgery can be facilitated by use of the present invention. It should be pointed out that most urethral strictures are successfully treated by gradual urethral dilation using filiforms and followers or sounds of increasing size. Occasionally, however, very tight strictures of a fibrous nature require transurethral incision. For this purpose a urethrotome, which comprises a metal instrument having a small knife blade hidden within its tip, is frequently used. The blade can be advanced or withdrawn and as the blade is manipulated, the roof of the urethra is incised. Following the division of the stricture, a retention catheter is introduced. The device of the present invention enables the urethrotome to be inserted over the hollow filiform and subsequently when the urethrotome is removed, the filiform will remain as a guide to place the stylet and Councill catheter assembly without losing the course of the urethra.

It will be apparent from the foregoing that a considerable improvement is provided in the ease and safety of passing the catheter and the stylet over a filiform as compared to the awkward and potentially dangerous procedure of threadably connecting the filiform to the stylet. In addition, placement of the elongated filiform allows dilatation by a hollow plastic follower or a hollow metal sound, cystoscopic examination, direct view urethrotomy and the subsequent placement of a Councill catheter or the like.

It will be understood that changes may be made in the details of construction, arrangement and operation, without departing from the spirit of the present invention, especially as defined in the following claims.

I claim:

1. A urethral instrument system consisting of a filiform and a catheter stylet for passing a catheter through the urethra and into the bladder, said filiform comprising a thin elongated flexible hollow tube of uniform inner and outer diameter throughout its length having open distal and proximal ends, the proximal end being smoothly contoured, tapered and curved so as to readily pass through the urethra and into the bladder, and said stylet comprising an elongated hollow tube having a uniform inner diameter that is slightly larger than the outer diameter of the filiform, open distal and proximal ends, the proximal end being smoothly contoured and the distal end including means for holding the catheter on the stylet, said urethral instrument system being structured such that after the filiform is passed through the urethra and into the bladder, the stylet inserted within the catheter can be slidably passed coaxially over said filiform thereby passing said catheter through the urethra into the bladder.

2. A urethral instrument as claimed in claim 1 wherein said means for holding the catheter on the stylet includes a barrel-shaped portion at the distal end of the stylet for insertion within the distal end of the catheter, the diameter of said barrel-shaped portion being slightly less than the inside diameter of the distal end of the catheter.

3. A urethral instrument as claimed in claim 2 wherein said barrel-shaped portion includes at least one annular ring formed thereon for engaging the inner wall of the distal end of the catheter.

4. A urethral instrument as claimed in claim 2 wherein said means for holding the catheter on the stylet further includes an annular projection formed about the proximal end of the stylet for engaging the inner wall of the proximal end of the catheter.

5. A urethral instrument as claimed in claim 1 including means for gripping the stylet at the distal end thereof, said gripping means comprising a cylindrical member with at least one flat side.

6. A urethral instrument as claimed in claim 1 wherein said stylet has a length greater than the distance between the entrance to the urethra and the bladder.

7. A urethral instrument as claimed in claim 1 wherein the proximal end is curved.

8. A urethral instrument as claimed in claim 1 wherein said filiform comprises a one-piece member having a length greater than the distance between the entrance to the urethra and the bladder plus the length of the stylet.

9. A method for passing a urethral instrument system as claimed in claim 1 through the urethra and into the bladder comprising:
(a) inserting the proximal end of a thin elongated flexible hollow filiform having (i) an opening near the proximal end, the proximal end being smoothly contoured, tapered and curved so as to readily pass through the urethra and into the bladder, (ii) a uniform inner and outer diameter and (iii) an open distal end, through the urethra until the proximal end enters the bladder and fluid drains through the opening and out the open distal end;
(b) sliding an elongated hollow stylet within a catheter coaxially over said filiform until the distal end of the filiform is exposed through the stylet, and the proximal end of the catheter and the stylet enters the bladder, said stylet having a uniform inner diameter that is slightly larger than the outer diameter of the filiform, open proximal and distal ends, the proximal end being smoothly contoured and the distal end including means for holding the catheter on the stylet;
(c) pulling the distal end of the stylet and the filiform which extend beyond the distal end of the catheter to withdraw the stylet and the filiform from the catheter and leave the catheter extending through the urethra and into the bladder.

10. A method as claimed in claim 9 wherein the filiform is reinserted through the catheter and the catheter is withdrawn from the urethra leaving the filiform in the bladder and subsequently slidably inserting other hollow urological instruments over the filiform.

11. A urethral instrument system comprising a filiform and a dilator for passing through the urethra and into the bladder, said filiform comprising a thin elongated flexible hollow tube having an open distal end and a smoothly contoured, tapered and curved proximal end which can be readily passed through the urethra and into the bladder, said filiform having an opening in the side thereof near the proximal end for the drainage of fluid to indicate that the filiform has reached the bladder, and said dilator comprising an elongated hollow tube having (a) open distal and proximal ends, the proximal end being smoothly contoured and (b) a uniform inner diameter that is slightly larger than the outer diameter of the filiform,
said urethral instrument being structured such that after the filiform is passed through the urethra and into the bladder said dilator can be slidably passed coaxially over said filiform to dilate the urethra.

12. A urethral instrument as claimed in claim 11 including a filiform stylet comprising an elongated solid member having an outer diameter slightly less than the inner diameter of the filiform to permit inserting the stylet within the filiform to stiffen the filiform to facilitate the passage of the filiform through the urethra.

13. The instrument of claim 11 wherein the hollow tube of the filiform has a substantially uniform inner diameter to accomodate the insertion and removal of a wire stylet within the filiform.

14. A method for passing a urethral instrument system through the urethra and into the bladder comprising:
(a) inserting a contoured proximal end of a thin elongated flexible hollow filiform having substantially uniform inner and outer diameters, an open distal end shaped for easy insertion through the urethra and into the bladder, and an opening in the side thereof near the proximal end through the urethra until the proximal end enters the bladder and fluid drains into the opening, through the filiform and out the open distal end thereby indicating that the filiform has reached the bladder;
(b) sliding an elongated hollow dilator having (1) open proximal and distal ends, the proximal end being smoothly contoured and (2) a uniform inner diameter that is slightly larger than the outer diameter of the filiform coaxially over said filiform until the proximal end of the dilator enters the bladder; and
(c) pulling the distal end of the filiform which extends beyond the distal end of the dilator to withdraw the filiform from the dilator.

15. A method as claimed in claim 14 further including the step (d) reinserting the filiform through the dilator, withdrawing the dilator from the urethra and slidably inserting a second dilator coaxially over said filiform as in steps (b) and (c).

16. A method as claimed in claim 15 wherein the dilator is instead withdrawn from the urethra leaving the filiform in the in the bladder and subsequently slidably inserting other hollow urological instrument coaxially over the filiform.

17. The method according to claim 14 wherein a wire stylet is inserted into said hollow filiform prior to insertion into the urethra, and wherein said stylet is removable to selectively permit fluid to drain through said hollow filiform.

* * * * *